US011318233B2

(12) United States Patent
Locke et al.

(10) Patent No.: US 11,318,233 B2
(45) Date of Patent: May 3, 2022

(54) APPARATUS AND METHOD FOR IDENTIFYING ALTERNATIVE CELL CHEMISTRIES FOR BATTERIES

(71) Applicant: KCI Licensing, Inc., San Antonio, TX (US)

(72) Inventors: Christopher Brian Locke, Bournemouth (GB); Richard Daniel John Coulthard, Verwood (GB); David Robson Blandford, Fordingbridge (GB)

(73) Assignee: KCI Licensing, Inc., San Antonio, TX (US)

( * ) Notice: Subject to any disclaimer, the term of this patent is extended or adjusted under 35 U.S.C. 154(b) by 836 days.

(21) Appl. No.: 16/195,470

(22) Filed: Nov. 19, 2018

(65) Prior Publication Data

US 2019/0134278 A1    May 9, 2019

Related U.S. Application Data

(62) Division of application No. 14/151,459, filed on Jan. 9, 2014, now Pat. No. 10,159,770.

(60) Provisional application No. 61/778,012, filed on Mar. 12, 2013.

(51) Int. Cl.
| | | |
|---|---|---|
| *A61M 1/00* | (2006.01) | |
| *G01R 31/385* | (2019.01) | |
| *G01R 31/378* | (2019.01) | |
| *H01M 10/42* | (2006.01) | |
| *H01M 10/48* | (2006.01) | |

(52) U.S. Cl.
CPC ......... *A61M 1/0023* (2013.01); *G01R 31/378* (2019.01); *G01R 31/386* (2019.01); *H01M 10/4221* (2013.01); *H01M 10/48* (2013.01)

(58) Field of Classification Search
CPC . A61M 1/0023; G01R 31/386; G01R 31/378; H01M 10/4221; H01M 10/48
USPC .......................................................... 324/426
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Andrew J Mensh (57) ABSTRACT

New and useful systems, methods, and apparatuses for automatically identifying alternative cell chemistries of batteries that power portable electric devices and adjusting the characteristics of such devices in response to the identification of such cells in a reduced-pressure therapy environment are set forth in the appended claims.

12 Claims, 5 Drawing Sheets

(56) References Cited

U.S. PATENT DOCUMENTS

| | | |
|---|---|---|
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,181,102 B1 * | 1/2001 | Andrews ............... H02J 7/0045 320/106 |
| 6,241,747 B1 | 6/2001 | Ruff |
| 6,287,316 B1 | 9/2001 | Agarwal et al. |
| 6,345,623 B1 | 2/2002 | Heaton et al. |
| 6,404,154 B2 | 6/2002 | Marcinkiewicz et al. |
| 6,404,164 B1 * | 6/2002 | Bean ..................... H01M 10/44 320/106 |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0095096 A1 * | 5/2004 | Melton ............... H02J 7/00047 320/132 |
| 2008/0275327 A1 * | 11/2008 | Faarbaek ............ A61B 5/68335 600/382 |
| 2009/0189614 A1 * | 7/2009 | Crawford .............. H01M 10/48 324/430 |
| 2011/0092927 A1 * | 4/2011 | Wilkes .............. A61F 13/00059 604/304 |
| 2011/0288511 A1 * | 11/2011 | Locke .................... A61M 1/82 604/319 |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |

(56) References Cited

FOREIGN PATENT DOCUMENTS

| JP | 4129536 B2 | 8/2008 |
|---|---|---|
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

\* cited by examiner

APPARATUS AND METHOD FOR IDENTIFYING ALTERNATIVE CELL CHEMISTRIES FOR BATTERIES

RELATED APPLICATIONS

This application is a divisional of U.S. patent application Ser. No. 14/151,459, filed Jan. 9, 2014, now U.S. Pat. No. 10,159,770, which claims the benefit under 35 USC § 119(e), of the filing of U.S. Provisional Patent Application No. 61/778,012, filed Mar. 12, 2013, which is incorporated herein by reference for all purposes.

TECHNICAL FIELD

The present invention relates generally to medical wound care systems, and more particularly, to automatically identifying alternative cell chemistries of batteries that power such systems and adjusting characteristics of such system in response to the identification of the cell.

BACKGROUND

Clinical studies and practice have shown that reducing pressure in proximity to a tissue site can augment and accelerate growth of new tissue at the tissue site. The applications of this phenomenon are numerous, but is has proven particularly advantageous for treating wounds. Regardless of the etiology of a wound, whether trauma, surgery, or another cause, proper care of the wound is important to the outcome. Treatment of wounds with reduced pressure may be commonly referred to as "reduced-pressure wound therapy," but is also known by other names, including "negative-pressure therapy," "negative pressure wound therapy," and "vacuum therapy," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients. One of the common challenges involves the use of batteries for portable reduced-pressure systems. Although a device may use a standard battery size such as, for example, an AA cell or a rechargeable pack, a user or caregiver may select batteries having different cell chemistries that may affect the operation of the portable reduced-pressure device. The batteries may be primary cells such as, for example, alkaline or zinc carbon cells, or rechargeable batteries such as nickel-cadmium or lithium-ion batteries. Different battery chemistries are used to suit different applications such as those that provide for recharging or offer a higher performance profile. Although a reduced-pressure system may be optimized to work with one particular type of battery, there is a danger that a user or caregiver may not follow directions and insert the wrong type of battery that causes the reduced-pressure system to function improperly during the treatment of a patient. Even when a reduced-pressure system might be capable of operating when a different battery type is used, the system might have a lower performance that would be optimized if the correct battery were used.

Another common challenge when using batteries is how to provide a reliable method for "fuel gauging" or for determining the remaining charge in a battery. As different battery types have different discharge curves and different initial voltages, this task is often simplified to nothing more than to provide an alert when the voltage drops to a predetermined level when the battery is nearly completely discharged and needs to be recharged or replaced. For example, devices configured to utilize current embodiments of fuel gauging often have a voltage that reads close to 100% until the batteries are already 90% discharged.

In order to make such portable reduced-pressure systems powered by batteries more reliable and predictable, and to accommodate different battery chemistries in the same system, a simple and effective method for identifying the cell chemistry of a battery installed in a device is desirable to better control and operate electrical devices including reduced-pressure systems utilizing batteries. A method for enabling the devices to alter their characteristics to accommodate the batteries installed without negatively affecting the performance of the reduced-pressure system is also desirable to provide seamless reduced-pressure treatment to a patient.

SUMMARY

According to an illustrative embodiment, an apparatus for identifying the fuel-cell chemistry of a battery inserted into an electronic device is disclosed. The apparatus comprises a test circuit including a resistor and a switch electrically connected in series and having two electrical contacts adapted to be connected to the battery when inserted into the electronic device. The switch is actionable between an open position to provide an open circuit voltage ($V_O$) of the battery and a closed position to provide a load voltage ($V_L$) of the resistor. The apparatus may further comprise a computer having a program for determining whether the electronic device has been powered up by the battery, measuring the open circuit voltage ($V_O$) of the battery, measuring the load voltage ($V_L$) of the resistor, calculating a percent voltage drop ($V_L/V_O$) resulting from connecting the resistor to the battery, and using these three values in connection with an algorithm to determine the cell chemistry of the battery and provide a battery-identifier output signal.

The apparatus may further comprise a controller responsive to the battery-identifier output and adapted to selectively adjust a characteristic of the electronic device to function with the battery having a cell chemistry as identified by the battery-identifier output signal. The controller may adjust a characteristic of the electronic device to function with a battery having a lithium cell chemistry if $V_O$ is greater than or equal to 1.65V and $V_L$ is greater than or equal to $0.55V_O$. The controller may adjust a characteristic of the electronic device to function with a battery having a zinc carbon cell chemistry if $V_L$ is less than $0.45V_O$. The controller may adjust a characteristic of the electronic device to function with a battery having an alkaline cell chemistry if $V_L$ is less than $0.55V_O$ but greater than $0.45V_O$. The resistor may be a discrete component and may be tested only once to establish the load voltage ($V_L$).

According to another illustrative embodiment, a method for identifying the cell chemistry of a battery inserted into an electronic device is disclosed. The method comprises determining whether a battery has been inserted into the electronic device, determining whether the electronic device has been powered up by the battery having an open circuit voltage ($V_O$), and measuring the open circuit voltage ($V_O$)

of the battery. The method further comprises connecting a resistor across the battery, the battery having a load voltage ($V_L$) based on the resistance of the resistor and measuring the load voltage ($V_L$) of the resistor, and calculating a percent voltage drop ($V_L/V_O$) resulting from connecting the resistor to the battery. The method further comprises using the resulting values of the open circuit voltage ($V_O$), the load voltage ($V_L$), and the percent voltage drop ($V_L/V_O$) in connection with an algorithm to determine the cell chemistry of the battery.

The method may further comprise adjusting a characteristic of the electronic device to function with a battery having a lithium cell chemistry if $V_O$ is greater than or equal to 1.65V and $V_L$ is greater than or equal to $0.55V_O$. The method may further comprise adjusting a characteristic of the electronic device to function with a battery having a zinc carbon cell chemistry if $V_L$ is less than $0.45V_O$. The method may further comprise adjusting a characteristic of the electronic device to function with a battery having an alkaline cell chemistry if $V_L$ is less than $0.55V_O$ but greater than $0.45V_O$.

According to another illustrative embodiment, a system for treating a tissue site with reduced pressure is disclosed and comprises a dressing including a manifold for providing a reduced-pressure treatment space to the tissue site, a sealing member for sealing the manifold within the reduced-pressure treatment space, and a reduced-pressure interface coupled to the sealing member for providing reduced pressure to the manifold. The system further comprises a reduced-pressure source fluidly coupled to the reduced-pressure interface to provide reduced pressure to the manifold. The system further comprises a test circuit including a resistor and a switch electrically connected in series and having to electrical contacts adapted to be connected to the battery when inserted into the electronic device, the switch being actionable between an open position to provide an open circuit voltage ($V_O$) of the battery and a closed position to provide a load voltage ($V_L$) of the resistor.

The system or the test circuit may further comprise a computer having a program for determining whether the electronic device has been powered up by the battery, measuring the open circuit voltage ($V_O$) of the battery, measuring the load voltage ($V_L$) of the resistor, calculating a percent voltage drop ($V_L/V_O$) resulting from connecting the resistor to the battery, and using these three values in connection with an algorithm to determine the cell chemistry of the battery and provide a battery-identifier output signal. The system may further comprise a controller responsive to the battery-identifier output and adapted to selectively adjust a characteristic of the electronic device to function with the battery having a cell chemistry as identified by the battery-identifier output signal. The controller may adjust a characteristic of the electronic device to function with a battery having a lithium cell chemistry if $V_O$ is greater than or equal to 1.65V and $V_L$ is greater than or equal to $0.55V_O$. The controller may adjust a characteristic of the electronic device to function with a battery having a zinc carbon cell chemistry if $V_L$ is less than $0.45V_O$. The controller may adjust a characteristic of the electronic device to function with a battery having an alkaline cell chemistry if $V_L$ is less than $0.55V_O$ but greater than $0.45V_O$.

Other aspects, features, and advantages of the illustrative embodiments will become apparent with reference to the drawings and detailed description that follow.

Other features and advantages of the illustrative embodiments will become apparent with reference to the drawings and detailed description that follow.

BRIEF DESCRIPTION OF THE DRAWINGS

A more complete understanding of the present invention may be obtained by reference to the following Detailed Description when taken in conjunction with the accompanying Drawings set forth below wherein.

DETAILED DESCRIPTION

New and useful systems, methods, and apparatuses for automatically identifying alternative cell chemistries of batteries that power portable electric devices and adjusting the characteristics of such devices in response to the identification of such cells in a reduced-pressure therapy environment are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The exemplary embodiments may also be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
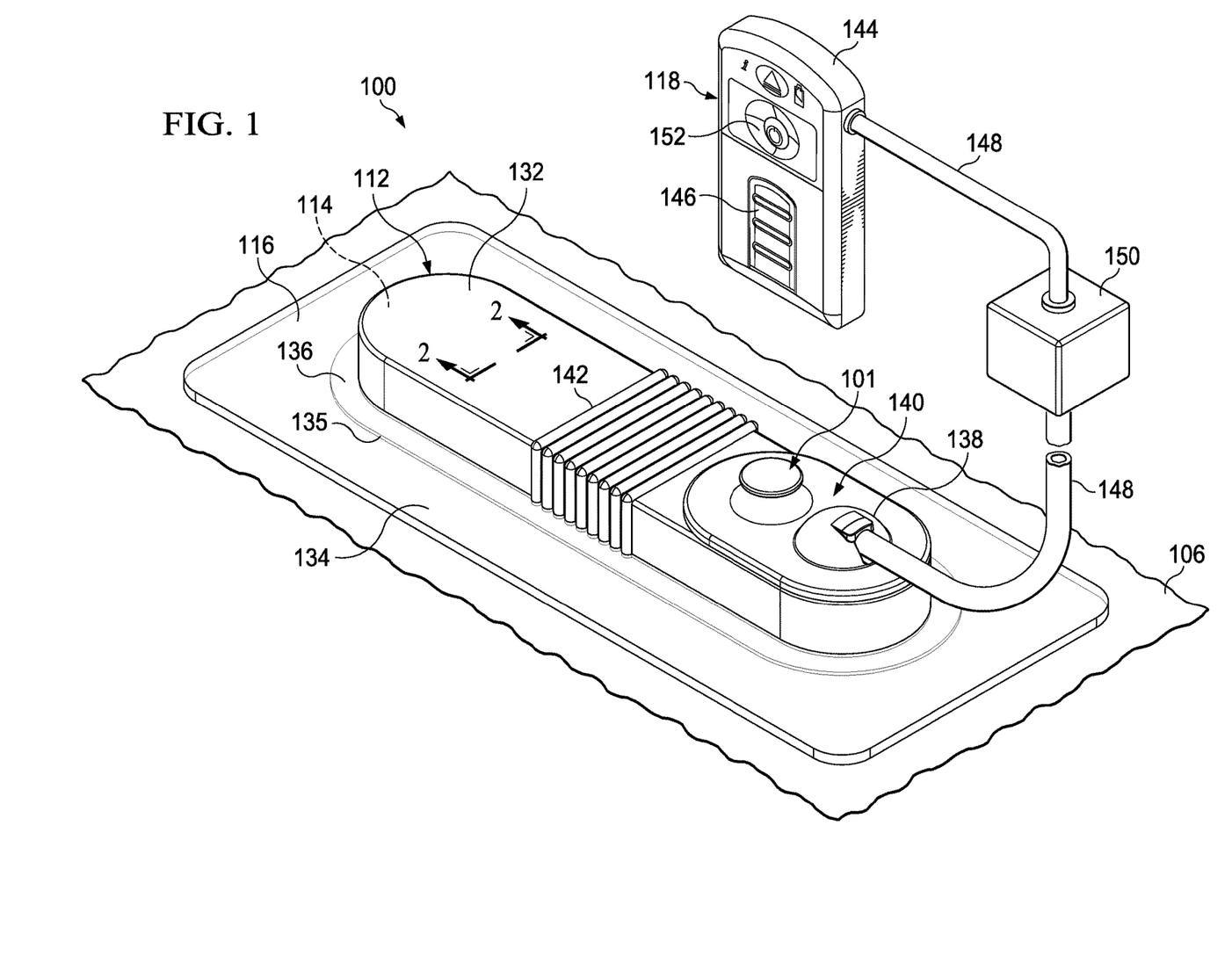
FIG. 1 is a perspective view of an illustrative embodiment of a reduced-pressure treatment system including a dressing for receiving reduced pressure from a source of reduced pressure.
Figure 2:
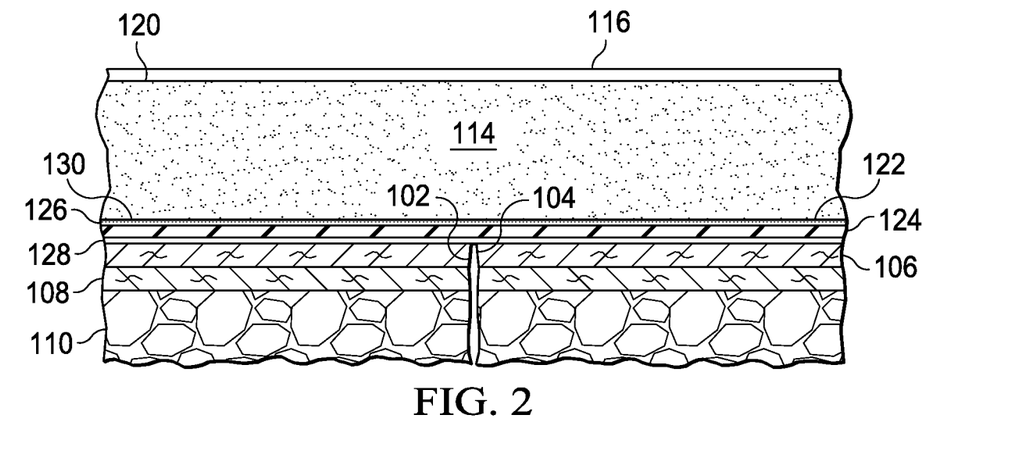
FIG. 2 is a cross section of a portion of the dressing of FIG. 1.

Referring primarily to FIGS. 1 and 2, an illustrative, non-limiting embodiment of a reduced-pressure treatment system 100 for treating a tissue site 102, such as a an incision 104, that includes a dressing reduced-pressure indicator 101 is presented. The incision 104 is shown extending through or involving epidermis 106, dermis 108, and subcutaneous tissue 110. The reduced-pressure treatment system 100 may also be used at other tissue sites. The reduced-pressure treatment system 100 includes a reduced-pressure dressing 112 having a flexible dressing bolster (shaped dressing bolster), or manifold member 114. In addition, the reduced-pressure treatment system 100 may include the sealing member 116 and a reduced-pressure subsystem 118. While the system 100 is shown in the context of a reduced-pressure dressing over an incision 104, it should be understood that the system 100 and the dressing reduced-pressure indicator 101 may be used on other tissue sites, including open wounds.

The flexible dressing bolster 114 has a first side 120 and a second, inward-facing side 122. The flexible dressing bolster 114 may be formed from any bolster material or manifold material that provides a vacuum space, or treatment space, such as a porous and permeable foam or foam-like material, a member formed with pathways, a graft, gauze, etc. As a more specific, non-limiting example, the flexible dressing bolster 114 may be a reticulated, open-cell polyurethane or polyether foam that allows good permeability of wound fluids while under a reduced pressure. One such foam material that has been used is the VAC® GranuFoam® material available from Kinetic Concepts, Inc. (KCI) of San Antonio, Tex. Any material or combination of materials may be used for the manifold material provided that the manifold material is operable to distribute the reduced pressure. The term "manifold" as used herein generally refers to a substance or structure that is provided to assist in applying reduced pressure to, delivering fluids to, or removing fluids from a tissue site A comfort layer 124, which has a first side 126 and a second, inward-facing side 128, may be coupled, e.g., by a heat bond 130 or any other technique, to the second side 122 of the flexible dressing bolster 114. The comfort layer 124 is typically to help provide for patient comfort when the flexible dressing bolster 114 is placed adjacent to the patient's epidermis 106. The comfort layer 124 may be any material that helps prevent skin irritation and discomfort while allowing fluid transmission through the comfort layer 124. As one non-limiting example, a woven, elastic material may be used or a polyester knit textile substrate. As another non-limiting example, an InterDry™ textile material from Milliken Chemical of Spartanburg, S.C., may be used. The comfort layer 124 may include anti-microbial substances, such as silver.

The sealing member 116 provides a fluid seal over the flexible dressing bolster 114 and at least a portion of the patient's epidermis 106. As such, the sealing member 116 may be formed from any material that provides a fluid seal. "Fluid seal," or "seal," means a seal adequate to maintain reduced pressure at a desired site given the particular reduced-pressure source or subsystem involved. The sealing-member 116 may be sealed against epidermis 106 or against a gasket or drape by a sealing apparatus, such as a pressure-sensitive adhesive. The sealing apparatus may take numerous forms, such as an adhesive sealing tape, or drape tape or strip; double-side drape tape; pressure-sensitive adhesive; paste; hydrocolloid; hydrogel; or other sealing means. The sealing member 116 may be an elastomeric material. "Elastomeric" means having the properties of an elastomer and generally refers to a polymeric material that has rubber-like properties. Sealing member materials may include a silicone drape, 3M Tegaderm® drape, or acrylic drape such as one available from Avery Dennison.

The sealing member 116 may include a first sealing member portion 132 and a second sealing member portion 134. The first sealing member portion 132 extends over the first side 120 of the flexible dressing bolster 114 and extends further to form a sealing member flange, or sealing member extension 136, which has a first side and a second, inward-facing side (not explicitly shown). An aperture is formed on a portion of the sealing member 116 to allow fluid communication with a reduced-pressure interface 138, which may be part of a reduced-pressure assembly 140. The second, inward-facing side of the sealing member extension 136 is placed on a first side (top side for the orientation of FIG. 1) of the second sealing member portion 134 and coupled, such as by an adhesive, bond 135, welding (e.g., ultrasonic or RF welding), cements, etc. Alternatively, the first sealing member portion 134 and second sealing member portion 136 may be integrally formed. The first sealing member portion 134 may include a plurality of bellows 142, folds, or stretch zones.

The reduced-pressure subsystem 118 includes a reduced-pressure source 144, which can take many different forms. The reduced-pressure source 144 provides reduced pressure as a part of the system 100. The reduced-pressure source 144 is fluidly coupled to the reduced-pressure interface 138 by a reduced-pressure delivery conduit 148. As used herein, "reduced pressure" generally refers to a pressure less than the ambient pressure at a tissue site 102 that is being subjected to treatment. In most cases, this reduced pressure will be less than the atmospheric pressure at which the patient is located. Alternatively, the reduced pressure may be less than a hydrostatic pressure at a tissue site. Unless otherwise indicated, values of pressure stated herein are gauge pressures. The reduced pressure delivered may be constant or varied (patterned or random) and may be delivered continuously or intermittently.

The reduced-pressure source 144 is shown having a reservoir region 146 or canister region. An interposed membrane filter, such as a hydrophobic or oleophobic filter, may be interspersed between the reduced-pressure delivery conduit 148 and the reduced-pressure source 144. One or more devices, such as a representative device 150, may be fluidly coupled to the reduced-pressure delivery conduit 148. The device 150 may be, for example, another fluid reservoir, or collection member to hold exudates and other fluids removed, a pressure-feedback device, a volume detection system, a blood detection system, an infection detection system, or a flow monitoring system The reduced-pressure source 144 may be any device for supplying a reduced pressure, such as a vacuum pump or other source. While the amount and nature of reduced pressure applied to a tissue site will typically vary according to the application, the reduced pressure will typically be between −5 mm Hg and −500 mm Hg and more typically in a therapeutic range between −100 mm Hg and −200 mm Hg.

The reduced-pressure source 144 may also include a computer and a controller (not shown) that regulates the application of reduced pressure to a patient as prescribed according to a specific therapy. In one embodiment, the computer and controller may be separate devices wherein the computer provides output signals to the controller that regulates the application reduced pressure among other functions in response to output signals from the computer. The controller may also include an interface device 152 allowing a user or caregiver to adjust various parameters of the treatment as necessary. The controller may also control other functions within the reduced-pressure treatment system 100 including the operation of the other representative devices 150.

The reduced pressure developed by reduced-pressure source 144 is delivered through the reduced-pressure delivery conduit 148 to the reduced-pressure interface 138. The reduced-pressure interface 138 allows the reduced pressure to be delivered through the sealing member 116 to the flexible dressing bolster 114. In providing treatment with the system 100, it is desirable to know that reduced pressure of at least a certain threshold level is being delivered to the tissue site 102. The dressing reduced-pressure indicator 101 accomplishes this task. The dressing reduced-pressure indicator 101 may a separate unit fluidly coupled to the sealing member 116 such that pressure from within the sealed space of the sealing member 116 reaches the dressing reduced-pressure indicator 101 or may be associated with the reduced-pressure interface 138 as part of the reduced-pressure assembly 140.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients. One of the common challenges involves the use of batteries for portable reduced-pressure systems as described above. Although a device may use a standard battery size such as, for example, an AA cell or a rechargeable pack, a user or caregiver may select batteries having different cell chemistries that may affect the operation of the portable reduced-pressure device. The batteries may be primary cells such as, for example, alkaline or zinc carbon cells, or rechargeable batteries such as nickel-cadmium or lithium-ion batteries. Different battery chemistries are used to suit different applications such as those that provide for recharging or offer a higher performance profile. Although a reduced-pressure system may be optimized to work with one particular type of battery, there is a danger that a user or caregiver may not follow directions and insert the wrong type of battery that causes the reduced-pressure system to function improperly during the treatment of a patient. Even when a reduced-pressure system might be capable of operating when a different battery type is used, the system might have a lower performance that would be optimized if the correct battery were used.

For example, the reduced-pressure subsystem 118 may be designed to operate with lithium AA batteries which may be the best cells available for this particular electrical device. The controller is designed to work optimally with this type of cell chemistry and is configured around the terminal voltage and discharge characteristics of lithium-ion batteries. The reduced-pressure subsystem 118 will physically accept other cell chemistries and will operate with them, but some of the features and attributes of the reduced-pressure subsystem 118 will not work as well as they would with lithium cells because the terminal voltage and discharge characteristics are different for other cell chemistries. Consequently, the interface device 152 may alert a user or caregiver either too early or too late that the motor drive of the reduced-pressure source 144, for example, is different which could result in a slower time period for drawing down the pressure of the reduced-pressure dressing 112 and/or the proper determination of the pressure leak threshold.

In order to make such reduced-pressure systems powered by batteries more reliable and predictable, and to accommodate different battery chemistries in the same system, a simple and effective method for identifying the cell chemistry of a battery installed in a device is desirable to better control and operate reduced-pressure systems utilizing batteries. A method for enabling the devices to alter their characteristics to accommodate the batteries installed without negatively affecting the performance of the reduced-pressure system is also desirable to provide seamless reduced-pressure treatment to a patient. For example, such a method may be used to allow the controller to alter software algorithms and thresholds to better match the limitations of the battery being used. The software may be updated to improve the operation of the reduced pressure system 100 in many ways such as, for example, by varying the aggression of the motor drive of the reduced-pressure source 144 to achieve a faster time period for drawing down the pressure of the reduced-pressure dressing 112, or altering the brightness of the brightness of the display of the interface device 152, or changing the thresholds for the alarm settings such as the leakage pressure for the reduced-pressure dressing 112 and blockages in the reduced-pressure delivery conduit 148.

Figure 3:
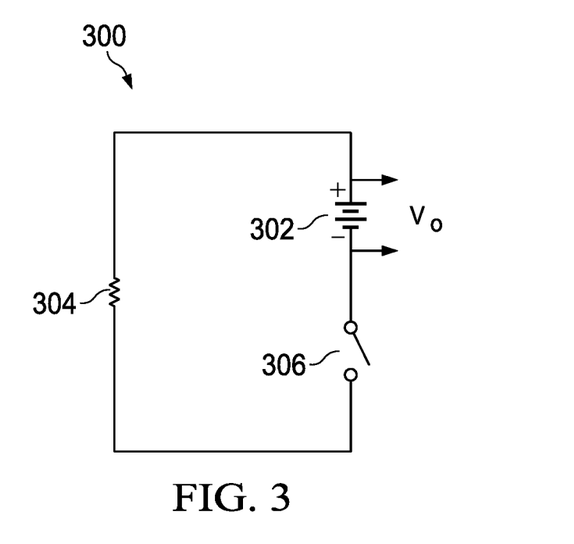
FIG. 3 is a schematic of an illustrative embodiment of a test circuit used to determine the identity of the cell chemistry of a battery that may be used in the reduced-pressure treatment system of FIG. 1.

FIG. 3 is a schematic of an illustrative embodiment of a test circuit used to determine the identity of the cell chemistry of a battery that may be used in the reduced-pressure treatment system 100. In this embodiment, the test circuit 300 includes the cell 302 to be tested, a load 304, and a switch 306. The cell 302 may be placed in a holder having two electrical contacts from which the voltage of the cell 302 may be monitored by a voltmeter, a multi-meter, an oscilloscope, or any other suitable instruments. The load 304 in this embodiment is connected in series with the cell 302 and may be a resistive load such as a resistor. The resistance of the load 304 may be determined based on the number of cells 302 to be tested. In one example, the resistance of the load 304 is about 0.25 R for one cell 302. In another example, the resistance of the load 304 is about 0.5 R for two cells 302 in series. The switch 306 may be any suitable mechanical or electrical switches such as, for example, an electrically switched relay. When the switch 306 is turned to an open state, an open-circuit voltage ($V_O$) of the cell 302 is measured; when the switch is turned to a closed state, a load voltage ($V_L$) of the cell 302 is measured. Both of the open-circuit voltage ($V_O$) and the load voltage ($V_L$) may be provided as inputs to both the computer and the controller to commence a start-up software routine stored on the computer as described above and to the controller as necessary.

The cell chemistry may be identified in the start-up software routine of the computer or the controller and run each time the reduced-pressure subsystem 118 is powered up. The method described herein requires only two voltage measurements, a measurement of a single load voltage ($V_L$) for each cell 302 and a corresponding measurement of the open-circuit voltage ($V_O$) for the same cell 302, thus requiring only one load 304 for the measurements. The load 304 applied to the cells 302 was 0.25 R for each single cell 302 and that test was completed within three seconds. It should be understood that this method is applicable to batteries having two or more cells simply by altering the value of the load resistance; the method still requires only one resistor. The two measurements were taken for each of three different cells, and a percentage voltage-drop ($V_L/V_O$) was calculated for each cell 302 based on these two measurements. For example, these three values were determined for a lithium battery (e.g., Energizer Ultimate Lithium L91 FR6), an alkaline battery (e.g., Duracell Procell MN 1500 LR6), and a zinc carbon battery (e.g., GP Greencell 15G R6P) and are summarized in the following Table I:

TABLE I

Measurements for 1 sec. Load Times

| Battery Type | $V_O$ | $V_L$ | $V_L/V_O$ (%) |
|---|---|---|---|
| Lithium | 1.695 | 0.953 | 56.233 |
| Alkaline | 1.588 | 0.971 | 61.130 |
| Zinc Carbon | 1.593 | 0.677 | 42.527 |

Figure 4A:
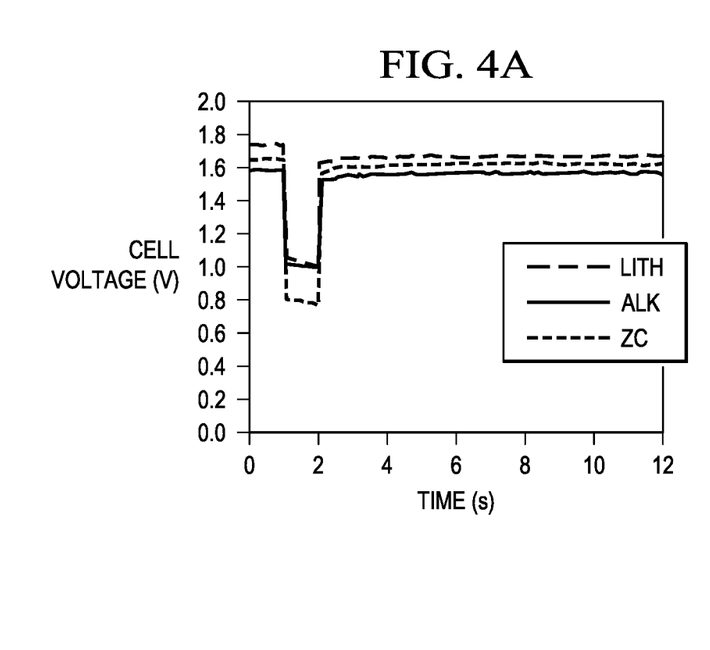
FIG. 4A is a graph illustrating the open circuit and load voltages being toggled over a one second time period for three different cell chemistries including lithium, alkaline, and zinc carbon.
Figure 4B:
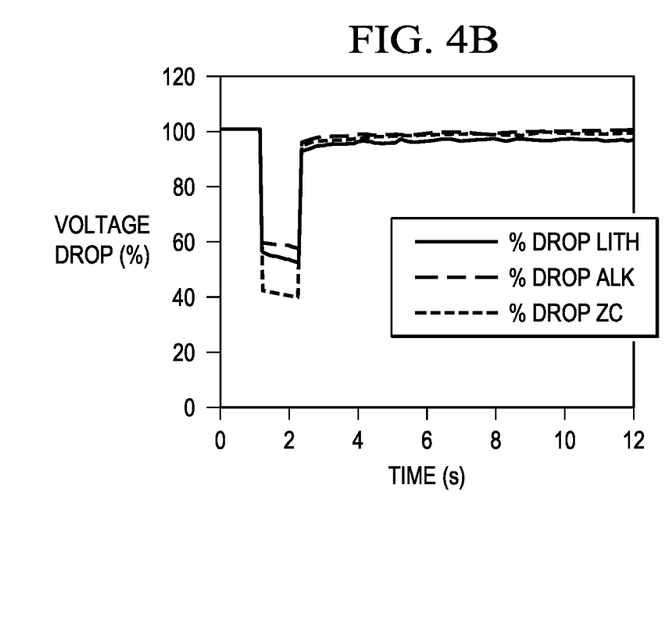
FIG. 4B is a graph illustrating the percent voltage drop from the open circuit voltages to the load voltages for the voltages measured and illustrated in FIG. 4A for the same three cell chemistries.

FIG. 4A is a graph illustrating the open circuit and load voltages being toggled over a one second time period for three different cell chemistries including lithium, alkaline, and zinc carbon. FIG. 4B is a graph illustrating the percent voltage drop from the open circuit voltages to the load voltages for the voltages measured and illustrated in FIG. 4A for the same three cell chemistries.

Based on these values, the cell chemistry may be identified based on the following set of rules, again assuming a load of 0.25 R as follows: (1) if $V_O$ is greater than or equal to 1.65V and $V_L$ is greater than or equal to $0.55V_O$, the cell chemistry is lithium; (2) if $V_L$ is less than $0.45V_O$, then the cell chemistry is a zinc carbon; and (3) if $V_L$ is less than $0.55V_O$ but greater than $0.45V_O$, the cell chemistry is alkaline. This algorithm yields reliable results with both new and used cells of a particular type of cell chemistry for a specific manufacturer. These rules may be implemented by a program stored on the computer of the reduced-pressure source 144 described above. The computer may provide an output signal, i.e., a battery-identifier output signal, to give the patient or caregiver a timely indication of the type of cell chemistry for the battery inserted into the reduced-pressure source 144. Additionally, the battery-identifier output signal may also be provided to the controller to automatically adjust characteristics of the reduced-pressure treatment system 100. For example, the controller may adjust the motor drive of the reduced-pressure source 144 in response to the battery-identifier output signal to warn a patient that an alkaline battery was used and to automatically increase the time period for drawing down the pressure of the reduced-pressure dressing 112 to compensate for the use of the alkaline battery.

Figure 5A:
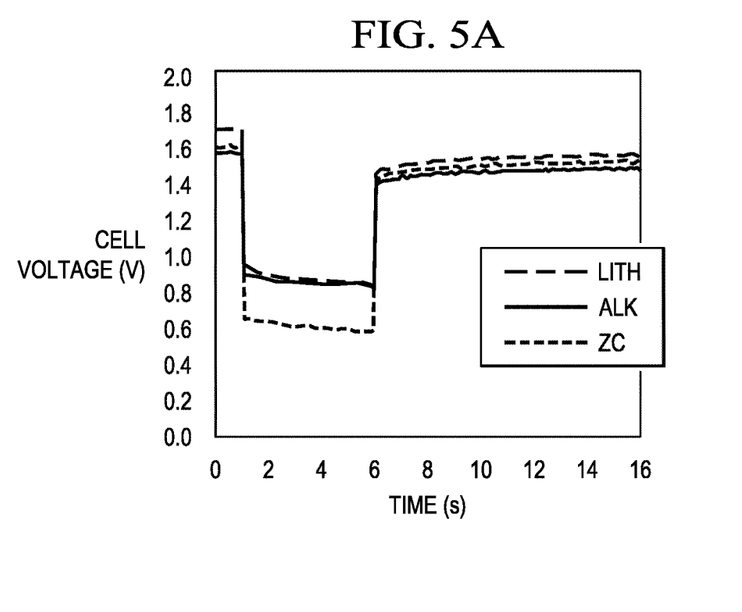
FIG. 5A is a graph illustrating the open circuit and load voltages being toggled over a five second time period for three different cell chemistries including lithium, alkaline, and zinc carbon.
Figure 5B:
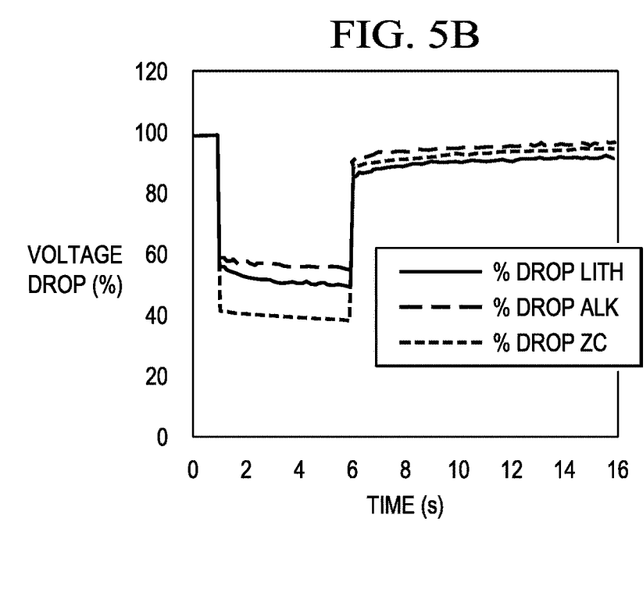
FIG. 5B is a graph illustrating the percent voltage drop from the open circuit voltages to the load voltages for the voltages measured and illustrated in FIG. 5A for the same three cell chemistries.

FIG. 5A is a graph illustrating the open circuit and load voltages being toggled over a five second time period for three different cell chemistries including lithium, alkaline, and zinc carbon. FIG. 5B is a graph illustrating the percent voltage drop from the open circuit voltages to the load voltages for the voltages measured and illustrated in FIG. 5A for the same three cell chemistries. Reviewing these graphs compared to FIGS. 4A and 4B makes it clear that the amount of time that the battery carries a load does not substantially affect the measurements of the open circuit voltage and the load voltage as described above. Thus, the method is accurate even when the battery is subject to load for only one second or less.

Figure 6:
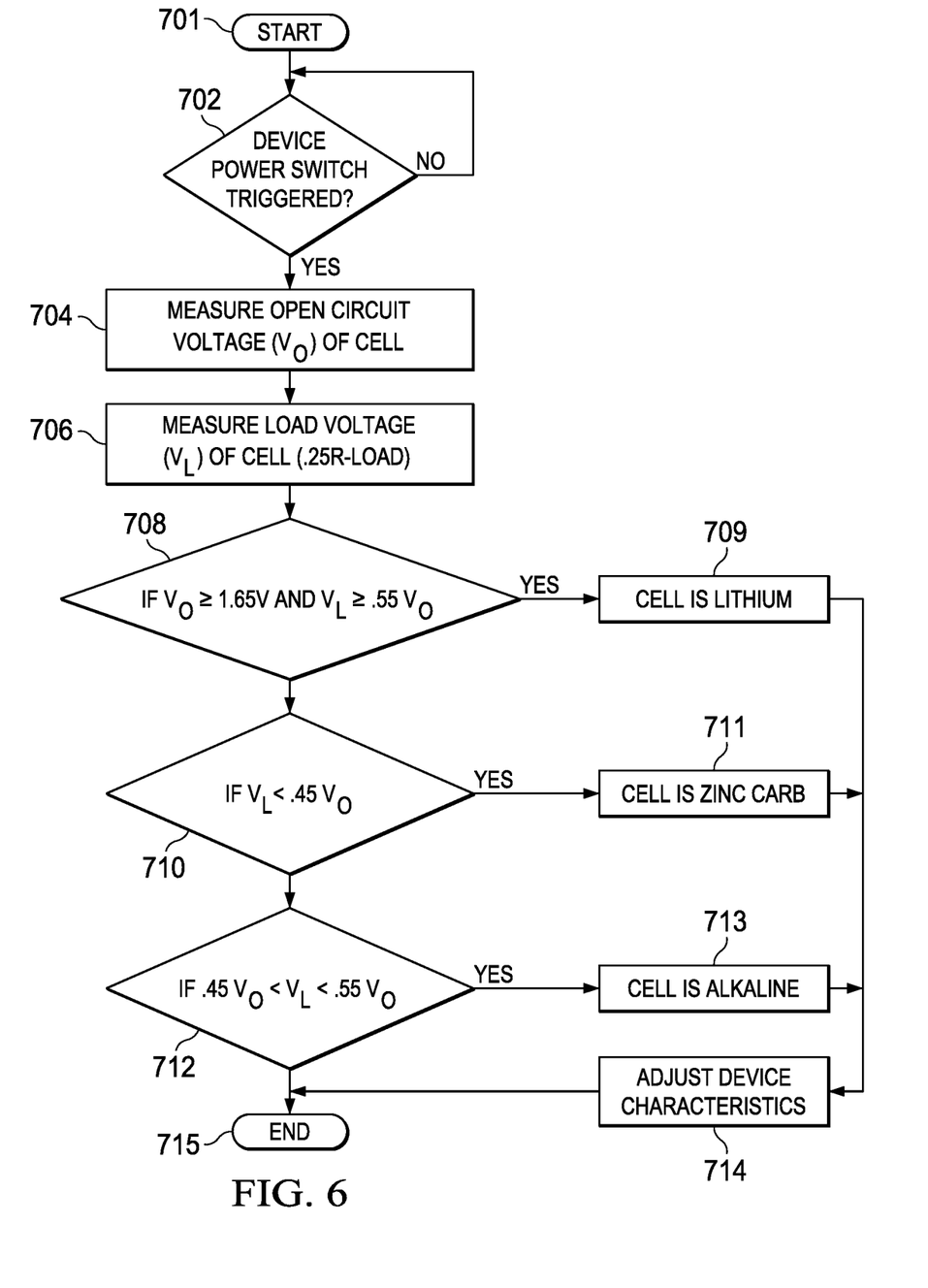
FIG. 6 is a flow diagram of a method for identifying the cell chemistry of a battery from among three different cell chemistries including lithium, alkaline, and zinc carbon.

FIG. 6 is a flow diagram of a method for identifying the cell chemistry of a battery from among three different cell chemistries including lithium, alkaline, and zinc carbon. In operation, the method starts at step 701 and proceeds to determine whether the device power switch has been triggered at step 702. More specifically, the method determines whether a battery has first been inserted into a portable electronic device and then whether the device has been powered up by the battery. If the device has been powered up by the battery, the process continues to step 704 where the open circuit voltage ($V_O$) of the battery is measured. As mentioned above, this may be performed by the test circuit 300 when the switch 306 is turned to the open state. Moving to step 706, the load voltage ($V_L$) of the battery is measured as described above, for example, for the one second time period as shown in FIGS. 4A and 4B. As mentioned above, this may be performed by the test circuit 300 when the switch 306 is turned to the closed state. In other words, the battery is serially connected to a resistor, and the voltage drop of the battery is measured. In one example, the resistance of the resistor is about 0.25 R for each cell of the battery.

After measuring the open circuit voltage ($V_O$) and the load voltage ($V_L$), the process proceeds with a series of comparisons to determine the type of cell chemistry of the battery that is been inserted into the portable electronic device. More specifically, if the open circuit voltage ($V_O$) is greater than or equal to 1.65V and the load voltage ($V_L$) is greater than or equal to $0.55V_O$ at step 708, then the process identifies the cell chemistry of the battery at step 709 as being lithium. If the load voltage ($V_L$) is less than $0.45V_O$ at step 710, then the process identifies the cell chemistry of the battery at step 711 as being zinc carbon. If the load voltage ($V_L$) is less than $0.55V_O$ but greater than $0.45V_O$ at step 712, the process than identifies the cell chemistry of the battery at step 713 as being alkaline. Of course, the series of comparisons at steps 708, 710 and 712 may be made in any order to identify the cell chemistry of the battery at any one of the steps 709, 711 and 713. In any event, the process utilizes such determination to adjust characteristics of the electronic device as shown at step 714 based on the specific identification of the cell chemistry of the battery. The adjustments include, but are not limited to, varying the aggression of the pump drive to achieve faster drawdown of dressings, altering the brightness and on-time of LCD displays, and changing thresholds for alarms, such as dressing leakage, low battery, tubing blockage, etc., as described above in more detail.

The systems and methods described herein may provide significant advantages, some of which have already been mentioned. For example, the operation and therapeutic treatment provided by reduced-pressure therapy systems powered by batteries may be more reliable and predictable for patients and caregivers.

It should be apparent from the foregoing that an invention having significant advantages has been provided. While shown in only a few forms, the systems and methods illustrated are susceptible to various changes and modifications without departing from the spirit and scope of the invention as described herein.

Although certain illustrative, non-limiting embodiments have been presented, it should be understood that various changes, substitutions, permutations, and alterations can be made without departing from the scope the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items. The steps of the methods described herein may be carried out in any suitable order, or simultaneously where appropriate.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A method for identifying the cell chemistry of a battery inserted into an electronic device for controlling a motor for driving a vacuum pump, the method comprising:
   inserting the battery into the electronic device wherein the battery contacts a test circuit comprising a resistor coupled in series with a switch, an input electrically coupled to terminals of the battery, and an output;
   opening the switch to measure an open circuit voltage ($V_O$);
   closing the switch to measure a load voltage ($V_L$);
   providing a battery-identifier output signal from the output from the test circuit including the open circuit voltage ($V_O$) and the load voltage ($V_L$);
   providing the battery-identifier output signal to a controller having an input coupled to the output of the test circuit and an output coupled to an input of a motor drive operatively coupled to the motor, the controller being responsive to the battery-identifier output signal to control the motor drive; and
   adjusting the aggression of the motor drive as determined by the cell chemistry of the battery and identified by the battery-identifier output signal.

2. The method of claim 1, further comprising measuring the open circuit voltage ($V_O$) of the battery, measuring the load voltage ($V_L$) of the resistor, calculating a percent voltage drop ($V_L/V_O$) resulting from connecting the resistor to the battery, and inputting these three values to an algorithm for determining the cell chemistry of the battery for providing the battery-identifier output signal.

3. The method of claim 2, further comprising using the algorithm to determine that the battery has a lithium cell chemistry if $V_O$ is greater than or equal to 1.65V and $V_L$ is greater than or equal to $0.55V_O$, and providing the battery identifier output signal to the controller for adjusting a characteristic of the electronic device to function with a battery having a lithium cell chemistry.

4. The method of claim 2, further comprising using the algorithm to determine that the battery has a zinc carbon cell chemistry if $V_L$ is less than $0.45V_O$, and providing the battery identifier output signal to the controller for adjusting a characteristic of the electronic device to function with a battery having a zinc carbon cell chemistry.

5. The method of claim 2, further comprising using the algorithm to determine that the battery has an alkaline cell chemistry if $V_L$ is less than $0.55V_O$ but greater than $0.45V_O$, and providing the battery identifier output signal to the controller for adjusting a characteristic of the electronic device to function with a battery having an alkaline cell chemistry.

6. Apparatus including an electric device for identifying the cell chemistry of a battery inserted into the electronic device for controlling a motor for driving a vacuum pump, the apparatus comprising:
   a motor drive having an input and an output operatively coupled to the motor;
   a test circuit including a resistor coupled in series with a switch and having an input configured to be connected to terminals of the battery when inserted into the electronic device, the switch being actionable between an open position to provide an open circuit voltage ($V_O$) of the battery and a closed position to provide a load voltage ($V_L$) of the resistor, the test circuit further having an output providing a battery-identifier output signal including the open circuit voltage ($V_O$) and the load voltage ($V_L$); and
   a controller having an input electrically coupled to the output of the test circuit and an output electrically coupled to the input of the motor drive, the controller being responsive to the battery-identifier output signal and configured to adjust the aggression of the motor drive as determined by the cell chemistry of the battery and identified by the battery-identifier output signal.

7. The apparatus of claim 6, wherein the test circuit comprises a computer having a program configured to measure the open circuit voltage ($V_O$) of the battery, to measure the load voltage ($V_L$) of the resistor, to calculate a percent voltage drop ($V_L/V_O$) resulting from connecting the resistor to the battery, and input these three values to an algorithm for determining the cell chemistry of the battery for providing the battery-identifier output signal.

8. The apparatus of claim 7, wherein the algorithm determines that the battery has a lithium cell chemistry if Vo is greater than or equal to 1.65V and $V_L$ is greater than or equal to $0.55V_O$ and provides the battery identifier output signal to the controller which adjusts a characteristic of the electronic device to function with a battery having a lithium cell chemistry.

9. The apparatus of claim 7, wherein the algorithm determines that the battery has a zinc carbon cell chemistry if $V_L$ is less than $0.45V_O$ and provides the battery identifier output signal to the controller which adjusts a characteristic of the electronic device to function with a battery having a zinc carbon cell chemistry.

10. The apparatus of claim 7, wherein the algorithm determines that the battery has an alkaline cell chemistry if $V_L$ is less than $0.55V_O$ but greater than $0.45V_O$ and provides the battery identifier output signal to the controller which adjusts a characteristic of the electronic device to function with a battery having an alkaline cell chemistry.

11. The apparatus of claim 6, wherein the battery comprises one or more cells (n), the resistor has a resistance of R, and when the switch is turned to the closed position, the resistor has a resistance of 0.25 R(n).

12. The apparatus of claim 6, wherein the load voltage ($V_L$) of the resistor is measured only once.

* * * * *